US008511165B2

(12) United States Patent
Lopez Jauregui

(10) Patent No.: US 8,511,165 B2
(45) Date of Patent: Aug. 20, 2013

(54) ELECTROMAGNETIC ACOUSTIC TRANSDUCER (EMAT) COMBINED WITH PIEZOELECTRIC TRANSDUCER (PZT) FOR DUAL MODE ULTRASONIC INSPECTION

(76) Inventor: Borja Lopez Jauregui, Bedford, VA (US)

( * ) Notice: Subject to any disclaimer, the term of this patent is extended or adjusted under 35 U.S.C. 154(b) by 352 days.

(21) Appl. No.: 13/071,444

(22) Filed: Mar. 24, 2011

(65) Prior Publication Data

US 2012/0240681 A1 Sep. 27, 2012

(51) Int. Cl.
*G01N 9/24* (2006.01)
(52) U.S. Cl.
USPC ............................. 73/643; 73/24.06; 381/338
(58) Field of Classification Search
USPC ................. 73/643, 24.06; 381/338
See application file for complete search history.

(56) References Cited

U.S. PATENT DOCUMENTS

| | | | | |
|---|---|---|---|---|
| 7,334,452 B2* | 2/2008 | Matsiev et al. | ............... | 73/24.06 |
| 8,090,131 B2* | 1/2012 | Lynnworth | ................... | 381/338 |
| 8,176,786 B2* | 5/2012 | Sohn et al. | ....................... | 73/602 |
| 2002/0092353 A1* | 7/2002 | Passarelli, Jr. | .................. | 73/643 |
| 2002/0134161 A1* | 9/2002 | Chinn | ............................ | 73/622 |
| 2004/0244490 A1* | 12/2004 | Turner | ............................ | 73/587 |
| 2008/0022773 A1* | 1/2008 | McKenna et al. | ............... | 73/597 |
| 2008/0072674 A1* | 3/2008 | Ume et al. | ...................... | 73/627 |
| 2008/0078249 A1* | 4/2008 | May | ............................... | 73/643 |
| 2009/0114022 A1* | 5/2009 | Reiderman | ..................... | 73/597 |
| 2009/0216467 A1* | 8/2009 | Andle | ............................ | 702/54 |
| 2012/0103097 A1* | 5/2012 | Lopez Jauregui | ............... | 73/643 |

* cited by examiner

Primary Examiner — Hezron E Williams
Assistant Examiner — Rodney T Frank

(57) ABSTRACT

An EMAT that generates horizontally polarized shear ultrasonic waves is combined with a PZT that generates longitudinal ultrasonic waves to provide simultaneous or sequential inspection of a test component material for improved accuracy in estimating properties of the material or detecting and estimating the dimensions of defects in the material. The transducer combination is constructed so that the EMAT and PZT elements are concentric and therefore interrogate approximately the same volume of the test component material. Nonferromagnetic insulators, such as elastomers, are installed on the bottom surface of PZT component to increase the transmission and reception the ultrasonic waves into the test component. Ferromagnetic, acoustic-absorbing materials are installed on the top surface of the EMAT coil component to minimize generation of ultrasonic waves in the bias magnet.

7 Claims, 9 Drawing Sheets

TOP VIEW

CROSSECTION A-A'

TOP VIEW

CROSSECTION A A'

TOP VIEW

CROSSECTION A A'

TOP VIEW

CROSSECTION A - A'

CROSSECTION A - A'

ELECTROMAGNETIC ACOUSTIC TRANSDUCER (EMAT) COMBINED WITH PIEZOELECTRIC TRANSDUCER (PZT) FOR DUAL MODE ULTRASONIC INSPECTION

TECHNICAL FIELD AND BACKGROUND OF THE INVENTION

This invention relates to methods and devices that are used for the excitation, transmission and reception of ultrasonic waves for non-destructive testing of various materials that are usually in the solid state. Nondestructive ultrasonic tests (UT) use very short acoustic waves that are composed of center frequencies typically in the range of 0.1 to 15 MHz and occasionally up to 50 MHz. Ultrasonic transducers convert electrical pulses into mechanical vibrations which are transmitted as beams of ultrasonic waves that propagate into said materials. Said ultrasonic waves reflect back to the transmitting transducer or are transmitted to other receiving transducers to produce electrical signals. Said signals are used to detect internal defects or to measure the chemical or physical properties of said materials.

UT is often performed on steel and other metals and alloys, although it can also be used on concrete, wood and composites, with some loss of sensitivity and resolution. UT is a method of nondestructive testing used in many industries including aerospace, automotive and transportation infrastructure such as pipelines and bridges. UT is frequently used to determine the thickness of the test component material, and therefore can be used to monitor defects such as corrosion in pipe. Also, it can be used to measure the metallurgical properties such as the nodularity of cast iron and physical properties such as the stress load on bolts.

Conventional UT is performed by using a transducer that is composed of a piezoelectric material to generate a compression wave, also known as a longitudinal (L) wave, as illustrated in FIG. 1. The L wave is generated by the abrupt application of a differential electrical potential to plates (1) and (2) through electrical conductors (3) and (4). When a positive voltage is applied to plate (1) a negative voltage or positive voltage of lesser magnitude is applied simultaneously to plate (2). This difference in electrical potential produces an electrical field that permeates the piezoelectric material (5) installed between the plates with the provision that said material is a poor electrical conductor, e.g. insulator. If said material exhibits piezoelectric properties, it will expand in the direction of its thickness by an amount that is proportional to the difference in the voltages applied to said plates. The thickness of said material decreases when the said electrical potentials are removed.

Application of a short electrical voltage pulse between plates (1) and (2) causes a rapid expansion and contraction of said material between said plates. Said rapid expansion and contraction of said material produces L waves that radiate acoustic energy in two directions, each being perpendicular to the plane of said plates. Said L waves (6) that radiate from the bottom plate (2) propagate through a coupling media (7) such as water, oil or rubber and into the test component (8) i.e. structure or part of a mechanism that is being interrogated. Reflections of said L wave from physical features or defects of said test component return to the transducer where they induce electrical signal responses by the reverse piezoelectric process, i.e., compression of piezoelectric material that produces electrical charges of opposite polarity on plates on the sides of said piezoelectric material. The electrical charges on said plates cause said electrical signals that can be observed at said electrical terminals connected to said plates. Said L waves that radiate from the top plate (1) are attenuated by damping material (9) to prevent penetration into the support backing material (10) and housing (11). Installation of said damping material eliminates the possibility of false indications and erroneous measurements caused by ultrasonic reflections within said backing material and housing.

Some UT applications require the use of shear waves instead of or in addition to said L waves. Although electric field transducers can be used to produce vertically polarized shear waves, the primary method of generating said shear waves results in a beam of energy that radiates at an angle that is less than 90 degrees with respect to the surface of the test material rather than a normal beam that is perpendicular to said surface. An alternate method of generating shear waves from piezoelectric transducers requires the use of viscous couplant such as honey or glue that has at least partial adhesion to the test component surface. The use of said viscous couplants for shear wave inspections is often a slow, tedious and costly process. Since many UT applications require the use ultrasonic waves that radiate from the transducers as normal beams, it is a valid conclusion that the use of piezoelectric transducers to generate shear waves for these applications is impractical for many applications.

An EMAT is the ideal transducer for many UT applications that require normal beam shear waves. FIG. 2 illustrates an EMAT composed of a circular spiral coil of insulated conductor such as copper wire (12) and a permanent magnet (13) which produces a relatively strong magnetic field, e.g., 5 kilogauss, in the test component and has a predominant component vector that is perpendicular to the test component surface. When an alternating current pulse is applied through lead wires (14) and (15) to said spiral coil an alternating magnetic field that encircles the windings of the coil is induced in the test component (8) in the immediate vicinity of said coil. Part of said induced magnetic field penetrates said test material and induces eddy currents (16) and (17) that flow in a solenoidal path and in a direction that is opposite to the current in said coil. When current flows into the outside lead (15) of said coil the eddy currents will flow in a clockwise direction, looking down on said spiral coil. This is indicated by eddy current direction (16) out of the page and eddy current direction (17) into the page of FIG. 2.

Interaction of said magnetic field from said permanent magnet with said eddy currents produces alternating, horizontal, shear forces that move the lattice of said test material either away from or toward the center of said coil. Said alternating shear forces generate horizontal-polarized shear (SH) waves [19] near the surface of the test material that propagate in direction that is normal or perpendicular to said test material surface. To prevent the induction of said shear waves in said permanent magnet, a ferromagnetic material that also has relatively high electrical resistivity (18) is installed between said coil and the pole of said permanent that is next to said coil. The magnetic field is concentrated in said ferromagnetic material and therefore diminished in the pole of the magnet so that relatively weak eddy currents and resulting weak shear waves are generated in said magnet. Also, said ferromagnetic material serves as a shield from transient magnetic fields caused by reflections within said magnet. Said shielding can be enhanced by attaching a thin sheet of electrical conductor such as copper to the magnet pole.

Two basic methods of receiving the ultrasonic waves, pulse-echo method and through-transmission method, are frequently used for nondestructive testing. The pulse-echo method uses the transducer to transmit and receive said ultrasonic waves. Said pulse-echo method pertains to reflected ultrasonic wave that comes from an interface, such as the back wall of the object or an imperfection within the object that returns to said transducer. Said ultrasonic wave is recorded as a signal having an amplitude that is proportional to the intensity of the reflected wave and with a time of arrival that is proportional to the travel distance of said reflection. In the attenuation or through-transmission method, a transmitter sends an ultrasonic wave through one surface, and a separate receiver on another surface detects and processes said ultrasonic wave that has reached said receiver after traveling through said test component. Imperfections or other conditions in the volume of test component material, which are located between the transmitter and receiver, change the characteristics of said ultrasonic wave, thus revealing their presence, location and in some cases physical characteristics within said component material.

SUMMARY OF THE INVENTION

The invention described herein is an ultrasonic transducer created by combining an EMAT with a PZT to form a transducer capable of generating, transmitting and receiving two acoustic wave modes. The EMAT part of the combination generates horizontal-polarized shear (SH) bulk waves that propagate in solid electrical conducting materials, e.g., metals, to be tested for physical and chemical property variations or defects. The PZT part of the combined transducer generates compression waves, i.e., longitudinal (L) waves, that propagate through an elastomer and into the component test material in a manner similar to that of said SH wave.

Said combination of EMAT with PZT provides either simultaneous or sequential nondestructive inspection with bulk SH waves and L waves that travel along the same path and in the same direction within the test component material. This configuration produces ultrasonic reflections back to the transducers or through transmissions to separate receivers that are affected by the same volume of material and the same variables within said volume of material. The electronic signals from said SH waves and L waves can be digitized and processed in combination by one or more computer algorithms to improve the accuracy of the ultrasonic test.

Acquisition and processing of SH and L wave signal serves as a means of improving the accuracy in the estimation of material properties or detection of defects by decreasing the signal response to unwanted variables in said same volume of said material. For example, said combination of EMAT and PZT can be used to improve the accuracy in estimating the percent nodularity in a cast iron test component without obtaining a secondary measurement of the thickness of said test component. Similarly, said combination of EMAT and PZT can be used to improve the accuracy in estimating the tensile load on a fastener bolt independent of the length of said bolt.

Said combination of EMAT and PZT is accomplished by integrating two basic transducer configurations. One integrated configuration is fabricated by etching printed circuit EMAT coils on a flexible insulating substrate so that coil conductors surround said PZT elements. A second configuration is fabricated by overlaying said EMAT coils on top of said PZT elements. Both configurations incorporate bias magnets, e.g., permanent magnets, which are placed over said EMAT coil conductors so that said magnets produce magnetic fields that are perpendicular to the surface plane of said test material component. A nonferromagnetic material, such as an elastomer, that exhibits minimal electrical conductivity is attached to bottom surface of each said PZT so that said L waves generated by each said PZT will be transmitted into said test material and said L wave reflections will be received by said PZT. A ferromagnetic backing material, such as a mixture of silicon rubber and iron particles, of appreciable incremental magnetic permeability, minimal electrical conductivity and substantial attenuation of said L waves is installed between said EMAT coil and said magnet so as to minimize the excitation and transmission of SH waves and L waves into said magnet. This backing material prevents said SH waves and L waves from entering into said magnet, reflecting from the physical boundaries of said magnet and being detected by said EMAT coils and PZT, thereby preventing false indications of changes in said properties or the occurrence of said defects in said test material component.

Another combined transducer design that provides simultaneous or sequential inspection with said SH waves and said L waves, is the combination of double-spiral EMAT coils, also referred to as butterfly coils. Said combination of EMAT and PZT is fabricated by etching two spiral printed circuit coils on each side of a flexible substrate, e.g., polyimide sheet. Said printed circuit coils are combined with rectangular PZT elements by etching printed circuit EMAT coils on a flexible insulating substrate such as a polyimide sheet so that coil conductors surround said PZT element or plurality of PZT elements. A second configuration of said combination of PZT and butterfly EMAT coil is fabricated by overlaying said butterfly coils on top of said PZT element or elements.

DETAILED DESCRIPTION OF THE INVENTION

Figure 1:
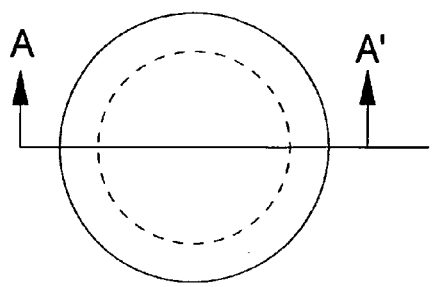
FIG. 1 illustrates the basic design and function of a PZT for generating and detecting L waves in various materials.
Figure 1:
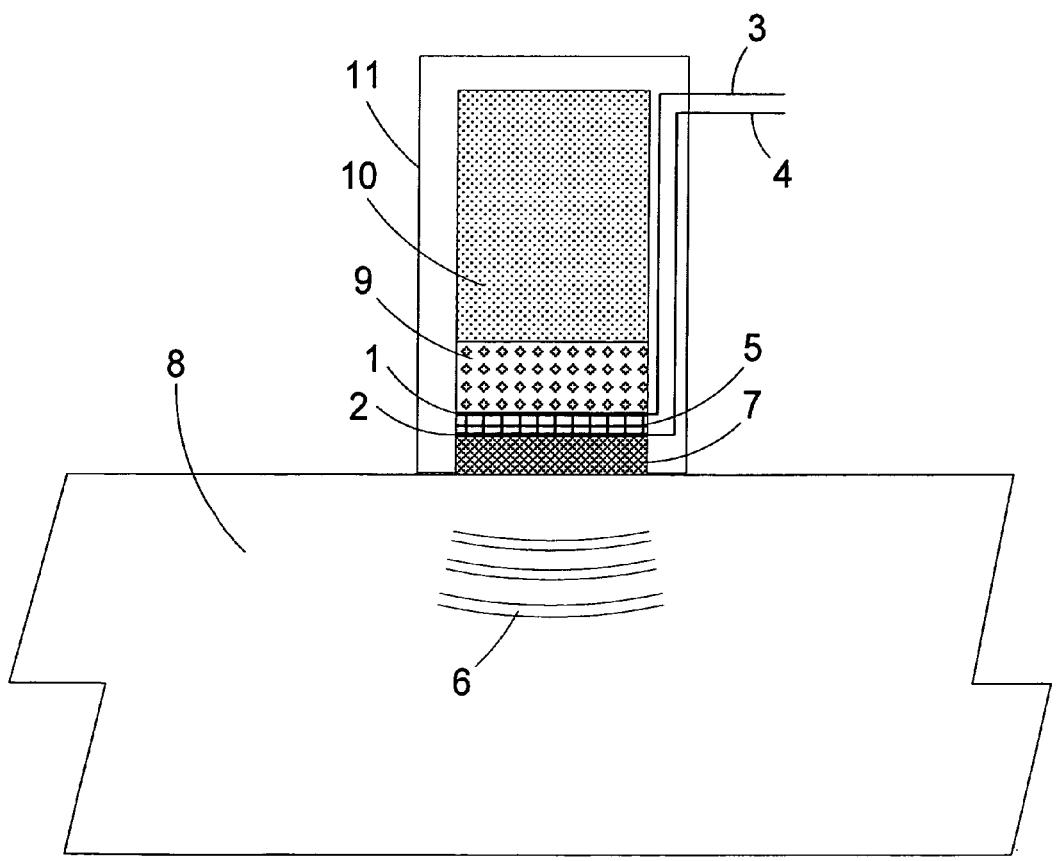
Figure 2:
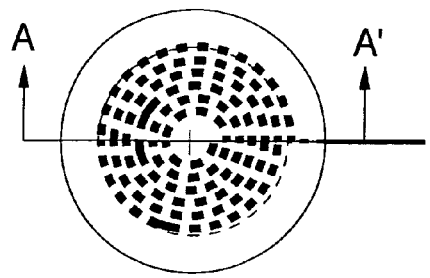
FIG. 2 illustrates the basic design and function of an EMAT for generating and detecting radially polarized SH shear waves in various materials.
Figure 2:
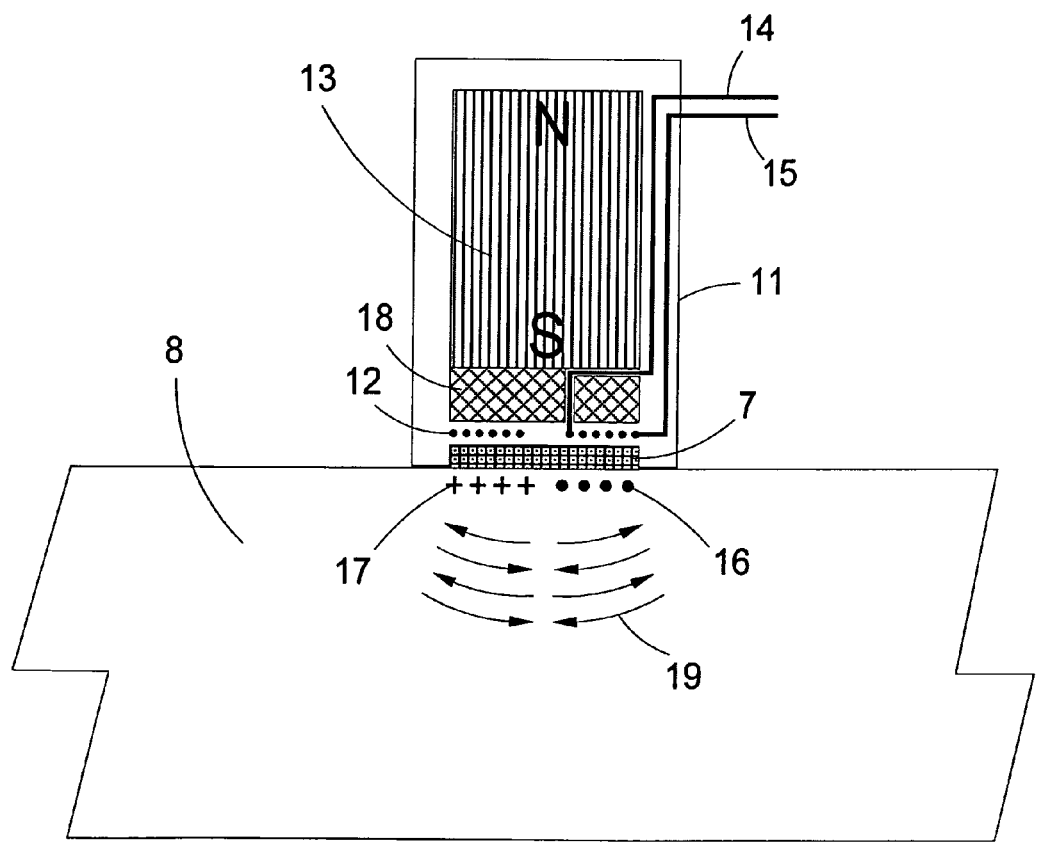

The disclosed invention pertains primarily to UT applications when it is desired or required to perform ultrasonic inspections by transmitting and receiving both L waves and shear waves in essentially the same direction and along the same path within a test component material. This dual-mode ultrasonic method interrogates the same volume of said test material by either receiving reflections from or transmissions through said test material of two different ultrasonic wave modes. Electronic signals corresponding to each of the said ultrasonic wave modes are processed, displayed and analyzed to estimate the properties and conditions of said test material. Said signal processing and analysis of said ultrasonic signals provide improved accuracy or classification of said materials in terms of said properties and conditions of said materials.

For example, the inspection of cast iron with both L waves and shear waves can result in a more accurate estimate of nodularity in cast iron components than by a method that uses either L waves or shear waves alone. Currently, either an L wave transducer or a shear wave transducer is used to measure the time-of-flight for either a reflection from a parallel surface or a transmission of the ultrasonic wave through a known thickness of said cast iron component. Said time-of-flight measurements are used to calculate the ultrasonic wave velocity which is proportional to the percent nodularity of the cast iron. Since the velocity of the ultrasonic wave is calculated by dividing said part thickness by the time-of-flight, the accuracy of the nodularity estimate is dependent on the accuracy of an independent thickness measurement. Since the thickness typically varies from cast iron part to part, a corresponding thickness measurement is required for each ultrasonic time-of-flight measurement in order to obtain the most accurate estimation of nodularity. Said thickness measurement is often tedious, slow and costly requiring that additional equipment, e.g., mechanical calipers, be integrated with the ultrasonic system and measurement process.

The requirement for an independent measurement of thickness of said casting in addition to the ultrasonic time-of-flight measurement to estimate nodularity can be eliminated by acquiring both an L wave and a shear wave measurement at the same position on said cast iron part. One means for accomplishing this is mathematically based on the two simultaneous equations derived from longitudinal wave and shear wave measurements of velocity that are acquired on cast iron samples of known nodularity. If a linear approximation between nodularity and said velocities is used, a set of two simultaneous equations that are functions of nodularity and thickness can be formed. A simple formula for nodularity in terms of the longitudinal and shear wave time-of-flight can be derived by solving said simultaneous equations. Even more accurate estimations of nodularity can be obtained by deriving nonlinear functions for predicting the degree of nodularity from mathematical tools such as regression analysis, neural network synthesis and pattern classifier software designs.

Measurement of stress, independent of acoustic path length, in a component part or structure is another nondestructive test that can be performed by the combination of L and shear wave time-of-flight measurements. For example, the accurate measurement of the tensile stress in a bolt, during and after assembly of a component such as a pressure vessel, is in many cases a critical factor in the continued safe operation of said component. Since the effective length of a bolt can vary from one threaded junction to another, the use of a either a longitudinal wave or a shear wave time-off-flight measurement to estimate tensile stress can result in considerable error. However, the simultaneous measurement of longitudinal and shear wave time-of-flight, provides for use of a formula similar to said formula derived for estimation of nodularity in cast iron component parts and structures. Said formula provides improved accuracy in estimating stress in said bolt by decreasing the affect of variations in bolt length.

Figure 3:
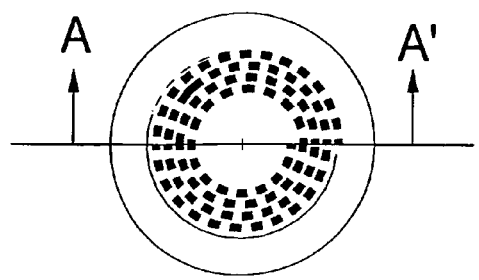
FIG. 3 illustrates the basic design and function of a Combination of PZT and EMAT for generating and detecting L waves and radially polarized SH waves in various materials.
Figure 3:
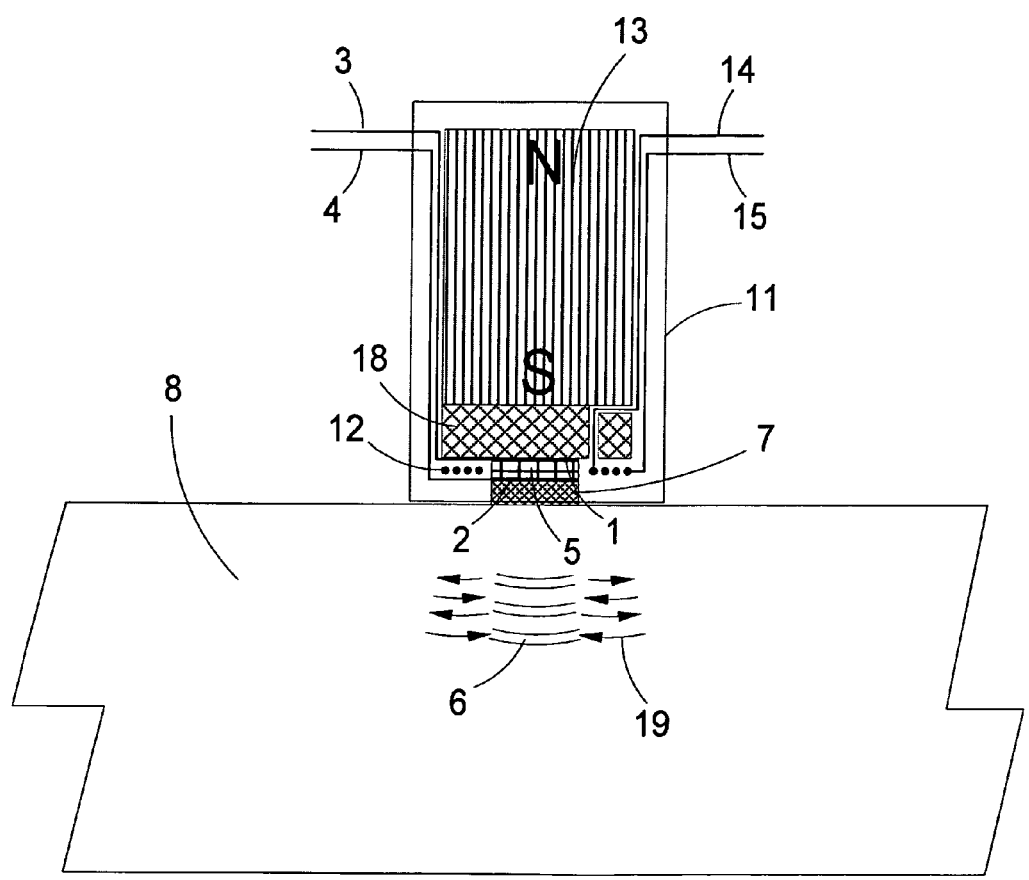

The disclosed invention is an ultrasonic transducer and associated electronic components composed of elements that enable simultaneous inspection with L waves and shear waves. As illustrated in FIG. 3, a piezoelectric material (5) is installed within housing (11) of said transducer, e.g., on the center of said transducer. Excitation of plates (1) and (2) on either side of said piezoelectric material with a differential voltage potential applied between electrical leads (3) and (4) causes said piezoelectric material to expand or contract depending on the polarity of the applied voltage and the properties of said piezoelectric material. A decrease or negative change in thickness of said piezoelectric material occurs when said voltage is decreased. Rapid variations in said applied voltage potential, e.g. at frequencies from 0.1 MHz to 100 MHz produce ultrasonic L waves that radiate from said upper plate, (1) and lower plate (2).

The circular spiral coil (12) surrounding said piezoelectric transducer is used to generate radially polarized, shear horizontal (SH) waves. Pulses of alternating current applied to lead wires (14) and (15) generate alternating magnetic fields that penetrate through coupling material (7) and induce eddy currents near the surface of the test component (8). Interaction of the eddy currents with the static field from permanent magnet (13) produce radially polarized shear waves (19) that propagate into said test component at an angle that is approximately 90 degrees to said test component surface. Reflections of said shear wave from defects internal to said test component or from the opposite surface of said test component are detected by the reverse process whereby the interaction of said acoustic waves with said static field from said permanent magnet induce eddy currents near the surface of said test material. Said eddy currents which are coupled electromagnetically to said circular spiral coil induce alternating signal voltages that can be detected at the terminals of lead wires (14) and (15).

Figure 4:
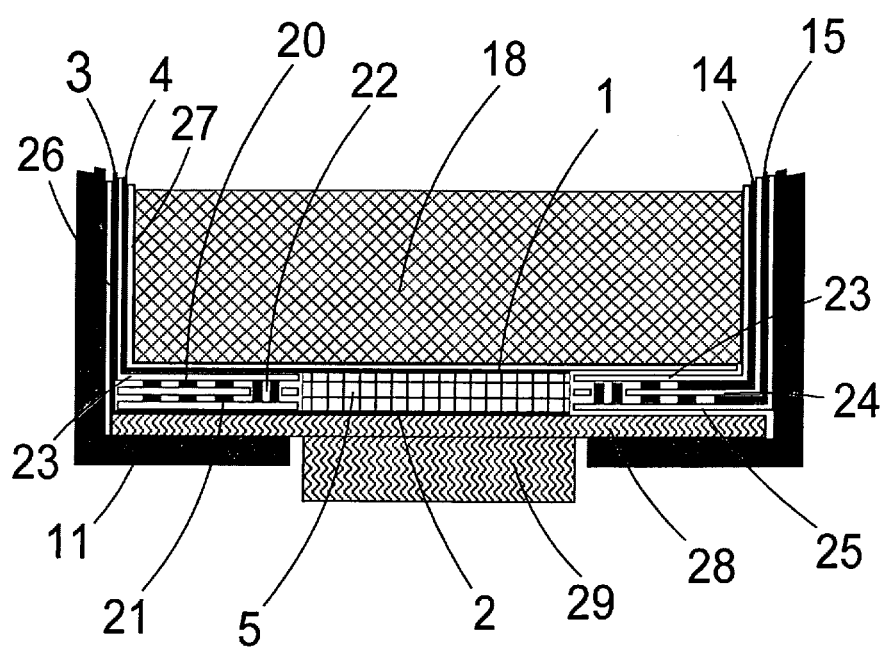
FIG. 4 is a crossection view the of a combination of concentric PZT and spiral EMAT coil for generating and detecting L waves and radially polarized SH waves in various materials.

The invention extensively incorporates the use of flexible printed circuit technology for reduced cost, consistent performance, improved reliability, low noise and greater sensitivity. FIG. 4 illustrates a cross-section view of a layered printed circuit construction in which a relative thin, piezoelectric disc is concentric with a spiral EMAT coil. The piezoelectric material consists of thin, durable, flexible materials that are compatible with flexible printed circuits. The plates (1) and (2) on either side of piezoelectric material are electrical conductor such as copper, aluminum or silver. The electrical leads (3) and (4) are composed of similar electrical conducting materials and are typically supported and insulated by cover layers of electrical insulation (23), (26) and (27). Said cover layers are thin sheets of flexible insulating material such as polyimide that are widely used in the fabrication of flexible printed circuits. Also, said cover layers provide the required electrical insulation between said leads of said PZT and the printed circuit conductors of the spiral EMAT coil (20) and (21) as well as backing material (18).

Ultrasonic L waves generated by said PZT are transmitted into the test component through a dry acoustic couplant material such as an elastomer, i.e., natural or synthetic rubber. Elastomers are the preferred choice for dry acoustic couplant material since they are flexible, compliant but not ferromagnetic. Synthetic elastomers provide superior performance for many applications since they have the potential for improved impedance matching to the piezoelectric materials and decreased acoustic attenuation as well as good flexibility and compliance. Said elastomers are applied in two layers (28) and (29) to enhance the compressibility and compliance to said test component. Layer (28) serves primarily as electrical insulation between said PZT and the housing (11). Elastomer layer (29), having a smaller area, exhibits greater compressibility and therefore increased coupling of said ultrasonic waves to said test component. Transducer housing (11) imposes a limit for the compression of said elastomer so that the time of travel of said L waves through said elastomer is relatively constant from test to test. Also, said elastomer (29)

is attached to elastomer (28) with adhesives which allow said elastomer to be easily replaced when excessive wear or damage to said elastomer occurs.

The backing material (18) that covers the top plate of the PZT absorbs most acoustic waves that are transmitted from said top plate. Also, said backing material is ferromagnetic, e.g., has a relative incremental magnetic permeability of ten or more, so that the magnetic fields generated by said EMAT coil are concentrated in said backing material and relatively little magnetic flux penetrates the permanent magnet. Careful design and selection of said backing material can provide negligible ultrasonic reflection signals of either L waves or SH waves within said magnet.

Figure 5:
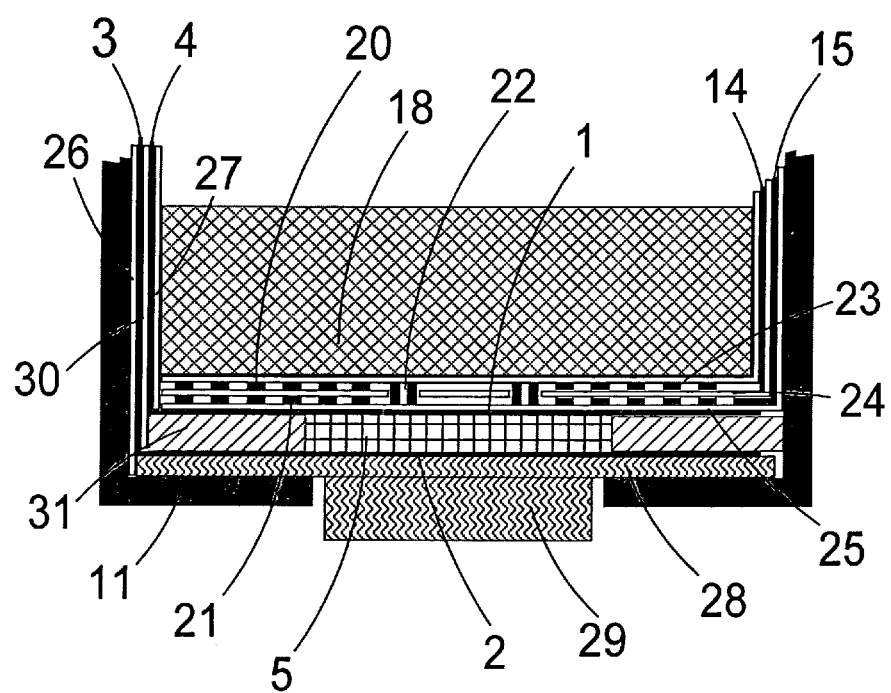
FIG. 5 is a crossection view of a overlaid combination PZT and EMAT coil for generating and detecting L waves and radially polarized SH waves in various materials.

Another construction for said combined PZT and SH EMAT is illustrated in FIG. 5. The PZT (5) with electrical conducting plates (1) and (2) cover approximately half of the permanent magnet diameter. Electrical leads (3) and (4) which connect said PZT plates to ultrasonic instrumentation are insulated from the housing (11), backing material (18) and each other by cover layers (26), (27) and (30) of electrical insulation such as polyimide. Elastomer (28) is attached to the bottom plate (2) of said PZT and elastomer (29) of smaller area is attached to said elastomer (28) to provide a path for transmission of the ultrasonic L waves into the test component material. The spiral EMAT coil, containing conductors on sides (20) and (21) of substrate (24) is installed on top of said PZT and may be attached to said top plate of said PZT. A part of the transient electromagnetic waves generated by said spiral coil penetrates said PZT and elastomer. Said transient electromagnetic waves couple to test component material and eddy currents are induced in said test component. Interaction between said eddy currents and the static magnetic field of the permanent magnet produce radial polarized shear waves that propagate into said test component in a direction that is normal to said component surface. Part of the L waves radiate from the top plate (1) of said PZT and propagate through said EMAT coil and into backing material (18). Also, said EMAT coils and insulating cover layers serve to damp said PZT and attenuate said part of said L waves radiating from said top plate.

Figure 6:
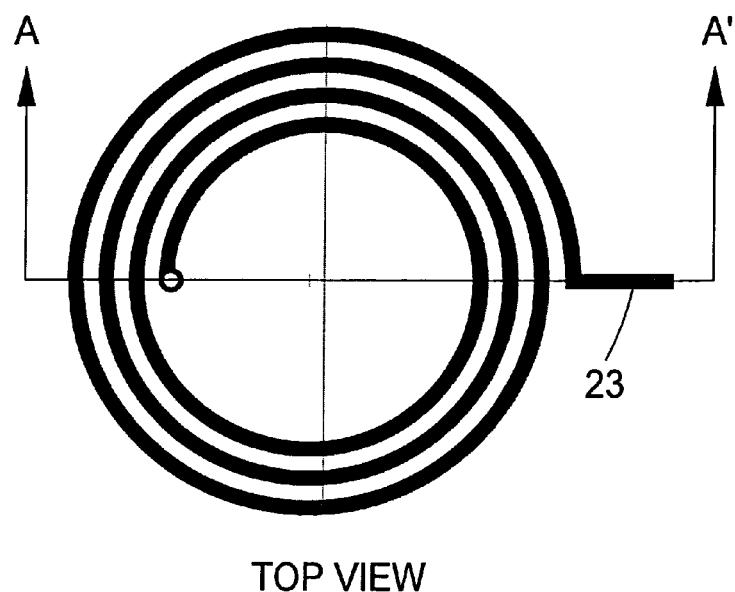
FIG. 6 is a view of the top layer and crossection of a spiral, printed-circuit, EMAT coil for generating and detecting radially polarized SH waves in various materials.
Figure 6:
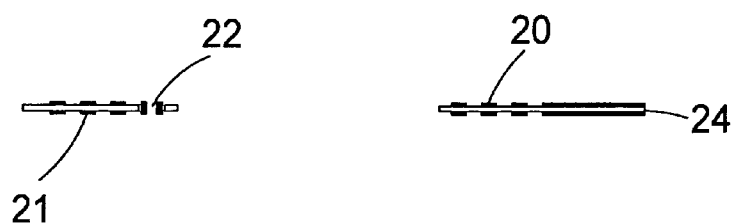

Said spiral coil is composed of two sides (20) and (21) of strips of electrical conducting material such as copper as illustrated in FIG. 6. Said conductor strips are etched on both sides of a flexible substrate (24) of electrical insulating material such as polyimide. When current is applied to the lead conductor (32) on the top surface (20) of said substrate, said current flows in a counter-clockwise direction looking down on said spiral coil, along said conductor into plated-through via (22). Said current then continues to flow through said via and along a spiral coil on said bottom side (21) of said substrate that is a mirror image of said coil on the top side of said substrate. Said current then flows in counter-clockwise direction into lead conductor (33) on said bottom side of said substrate.

Figure 7:
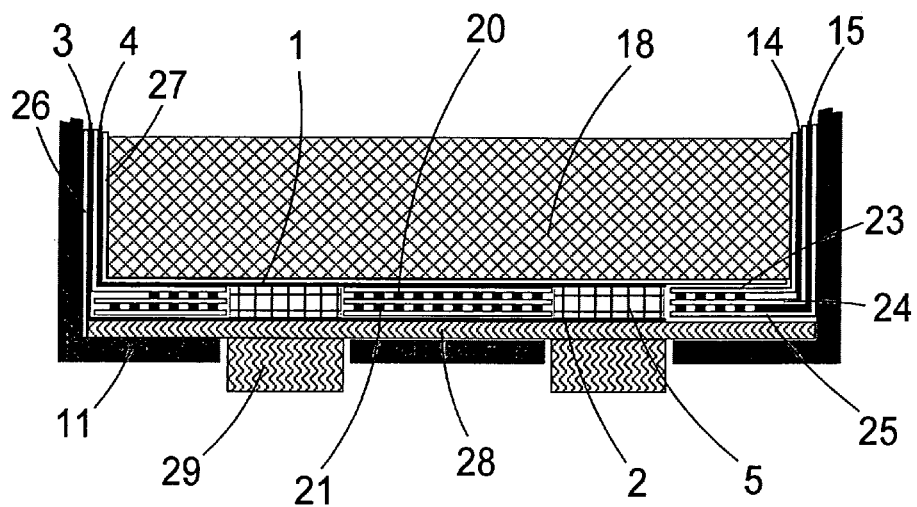
FIG. 7 is a crossection view of a combined, concentric PZT and EMAT butterfly coil for generating and detecting L waves and linearly polarized SH waves in various materials.
Figure 8:
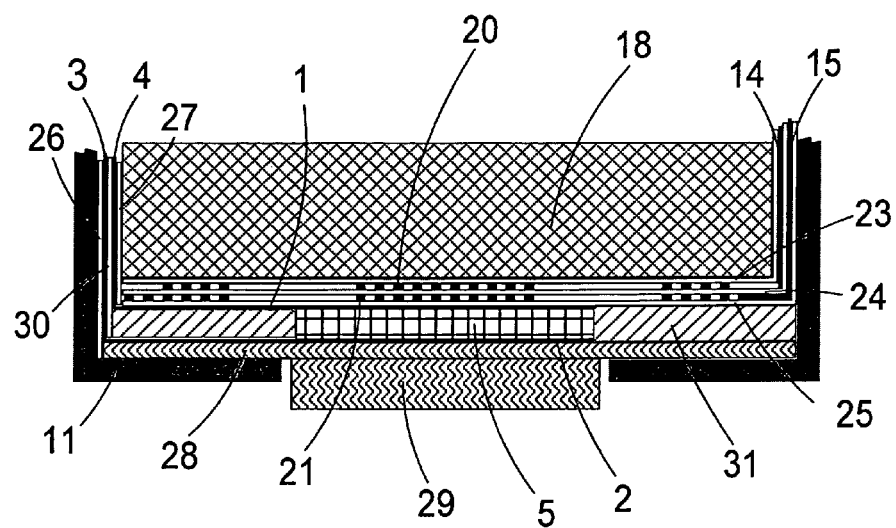
FIG. 8 is a crossection view of a combined, overlaid PZT and EMAT butterfly coil for generating and detecting L waves and linearly polarized SH waves in various materials.
Figure 9:
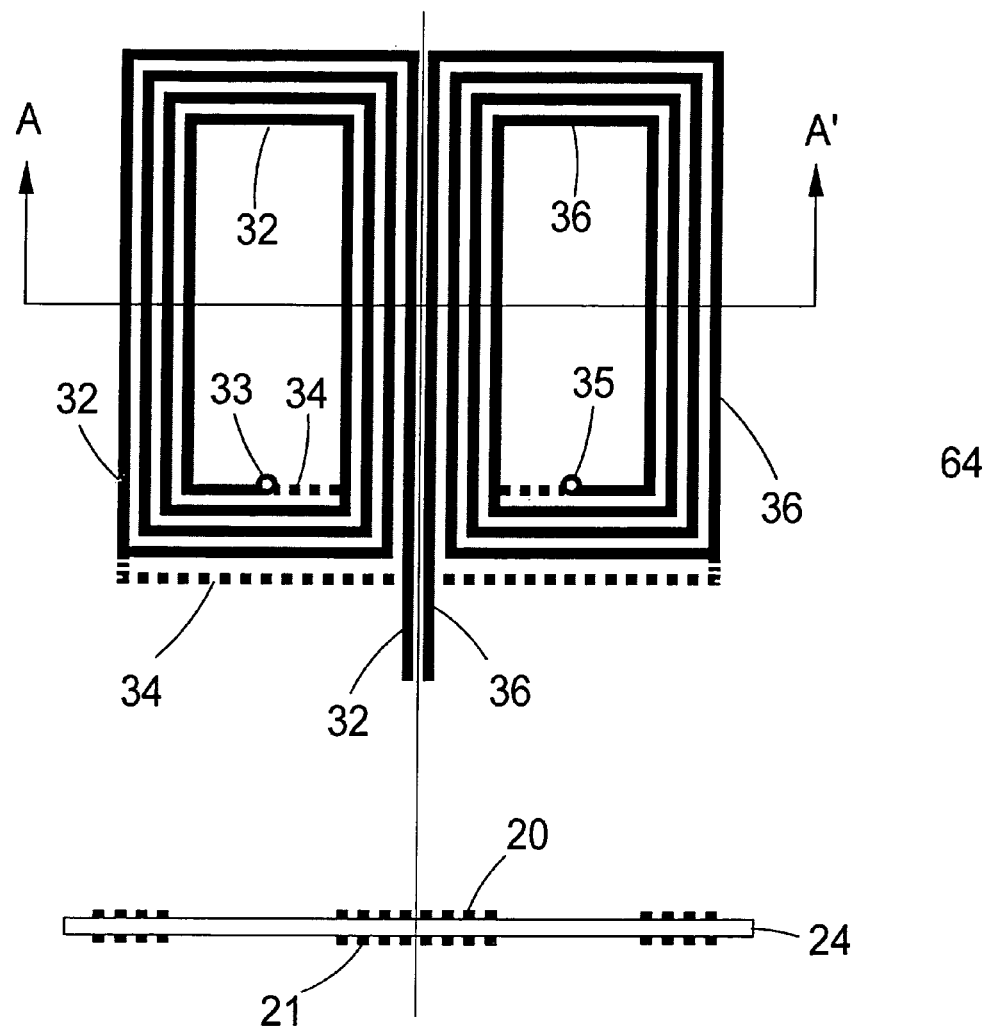
FIG. 9 is a view of the top layer and crossection of a butterfly, printed-circuit, EMAT coil for generating and detecting radially polarized SH waves in various materials.

The double-spiral or butterfly coil, as illustrated in FIG. 7, FIG. 8 and FIG. 9, is another EMAT configuration that can be combined with one or more PZT elements to facilitate simultaneous inspections with L waves and SH waves. Said butterfly coil EMAT is used extensively to produce a narrow ultrasonic beam of approximate rectangular crossection that propagates into a test component at an angle that is approximately normal to said test component entering surface. Said PZT elements can be combined with said butterfly coils by installing said PZT elements in the gaps between said butterfly coil windings, as illustrated in FIG. 7 or by installing said butterfly over said PZT, as illustrated in FIG. 8. Said PZT elements and Butterfly coils are electrically insulated from each other so that the combination of transducer elements can be used to transmit said ultrasonic L waves and SH waves either simultaneously or in sequence.

FIG. 8 illustrates a cross-section view of a layered printed circuit construction in which a rectangular, piezoelectric elements are concentric with each half of a double layered butterfly coil. The PZT consists of thin, durable, flexible materials that are compatible with flexible printed circuits. The plates (1) and (2) on either side of piezoelectric material can be any electrical conductor such as copper, aluminum or silver. The electrical leads (3) and (4) are composed of similar electrical conducting materials and are supported and insulated by cover layers of electrical insulation (23), (26) and (27), e.g., polyimide. Said cover layers are thin sheets of flexible insulating material that are widely used in the fabrication of flexible printed circuits. Also, said cover layers provide the required electrical insulation between said leads of said PZT and the printed circuit conductors of butterfly coil (20) and (21) as well as backing material (18).

Ultrasonic L waves generated by said PZT elements are transmitted into the test component through a dry acoustic couplant material such as an elastomer. Elastomers are the preferred choice for dry acoustic couplant material since they are flexible, compliant but not ferromagnetic. Said elastomers are applied in two layers (28) and (29) to enhance the compressibility and compliance to said test component. Layer (28) serves primarily as electrical insulation between said PZT and the housing (11). Elastomer layers (29), having a smaller area, exhibits greater compressibility and therefore increased coupling of said ultrasonic waves to said test component. Transducer housing (11) imposes a limit for compression of said elastomer so that the time of travel of said L waves through said elastomer layers is relatively constant from test to test. Also, said elastomers (29) are attached to elastomer (28) with adhesives which allow said elastomers to be easily replaced when excessive wear or damage to said elastomer occurs.

Another construction for said combined PZT and SH EMAT is illustrated in FIG. 9. The PZT (5) with electrical conducting plates (1) and (2) cover the center part of the butterfly coil and approximately half of the permanent magnet width. Electrical leads (3) and (4) which connect said PZT plates to ultrasonic instrumentation are insulated from the housing (11), backing material (18) and each other by cover layers (26), (27) and (30) respectively. Elastomer (28) is attached the bottom plate (2) of said PZT and elastomer (29) of smaller area is attached to said elastomer (28) to provide a path for transmission of the ultrasonic L waves into the test component material. The spiral EMAT coil, containing conductors on sides (20) and (21) is installed on top of said PZT and may be attached to said top plate of said PZT. A part of the transient electromagnetic waves generated by said spiral coil penetrate said PZT and elastomer and couple to test component material. Eddy currents are induced in said test component. Interaction between said eddy currents and the static magnetic field of the permanent magnet produce radially polarized shear waves that propagate into said test component in a direction that is normal to said component surface. Part of the L waves radiate from the top plate (1) of said PZT and propagate through said EMAT coil and into backing material (18). Said backing material attenuates said L waves and prevents penetration of said L waves into the magnet. Also, said EMAT coils and insulating cover layers serve to damp said PZT and attenuate said part of said L waves radiating from said top plate.

Said butterfly coil is composed of two sides (20) and (22) of strips of electrical conducting material such as copper, as illustrated in FIG. 9. Said strips are etched on both sides of a flexible substrate (24) of an electrical insulating material such as said polyimide. When current is applied to the lead conductor (32) on the top side (20) of said substrate, said current flows along the rectangular spiral on the left hand side of said butterfly coil in a counter-clockwise direction when looking down on said butterfly coil into plated through-hole via (33). Said current flows through plated-through hole along conductor (34) in the rectangular spiral coil on the bottom side (21) of said substrate in a counter-clockwise direction. Said current continues to flow in said conductor (34) and into the rectangular spiral coil on the right hand side of said butterfly coil on said bottom side of said substrate. Said current continues to flow along conductor (34) on said bottom side to of said substrate into via (35). Said current then flows through said via and into conductor (36). Said current continues to flow in a counter-clockwise direction along said conductor (36) and out of said butterfly coil.

The invention claimed is:

1. An EMAT combined with a PZT for purposes of generating shear waves and L waves that propagate in the same direction and along the same path in a test material component in order to estimate properties of said test material, measure dimensions of said test material, detect defects in said test material component and classify defects in said test material component.

2. A combination of EMAT and PZT as in claim 1 wherein said PZT is composed of thin piezoelectric material and plates of electrically conducting material such as copper, aluminum or silver attached to the top and bottom surfaces of said piezoelectric material.

3. A combination of EMAT and PZT as in claim 1 wherein an elastomer is attached to the bottom plate of said PZT for purposes of transmitting L waves into said test material and also for transmitting L waves reflected from features or defects internal to said test material to said PZT.

4. A combination of EMAT and PZT as in claim 1 wherein an acoustic absorbing material is attached to the top plate of said PZT for purposes of damping said PZT and attenuating said L waves that are generated by said PZT and transmitted toward the permanent magnet that is installed above and adjacent to said top plate of said PZT.

5. A combination of EMAT and PZT as in claim 1 wherein a circular, rectangular or other shaped spiral EMAT coil composed of two layers of printed circuit conductors, surrounds said PZT that is concentric with said spiral coil for purposes of generating shear waves that are transmitted into a test material component and for receiving shear waves reflected from features or defects internal to said test material component.

6. A combination of EMAT and PZT as in claim 5 wherein the top printed circuit layer of said EMAT coil is covered with a material that serves the dual purpose of attenuation of said ultrasonic L waves and shielding of transient magnetic fields from the permanent magnet by having an incremental magnetic permeability greater than 10.

7. A combination of EMAT and PZT as in claims 1, 2 and 3 wherein said EMAT is attached to the top of the PZT, said elastomer is attached to the bottom of said PZT and acoustic absorbing, ferromagnetic material is attached to the top said EMAT coil, between said coil and the permanent magnet.

* * * * *